(12) United States Patent
Seiwell

(10) Patent No.: US 8,827,075 B2
(45) Date of Patent: Sep. 9, 2014

(54) MOBILE MULTIPLE SYRINGE HOLDER

(71) Applicant: David Edward Seiwell, Snyder, TX (US)

(72) Inventor: David Edward Seiwell, Snyder, TX (US)

( * ) Notice: Subject to any disclaimer, the term of this patent is extended or adjusted under 35 U.S.C. 154(b) by 56 days.

(21) Appl. No.: 13/740,192

(22) Filed: Jan. 12, 2013

(65) Prior Publication Data

US 2014/0197120 A1 Jul. 17, 2014

(51) Int. Cl.
*A47F 7/00* (2006.01)
*B65D 83/10* (2006.01)
*A61M 5/00* (2006.01)

(52) U.S. Cl.
CPC .................................... *A61M 5/008* (2013.01)
USPC ........................... 206/366; 211/60.1; 206/443

(58) Field of Classification Search
USPC ......... 206/365, 366, 486, 490, 570, 571, 443; 211/60.1, 70.6, 74
See application file for complete search history.

(56) References Cited

U.S. PATENT DOCUMENTS

| | | | |
|---|---|---|---|
| 59,086 A | 10/1866 | Skinner | |
| 650,348 A | 5/1900 | Witkowski | |
| 759,588 A | 5/1904 | Baird | |
| 2,790,547 A | 4/1957 | Sutton | |
| 2,929,510 A | 3/1960 | Penn | |
| 3,116,730 A | 1/1964 | Tingley | |
| 3,348,894 A | 10/1967 | De Berry | |
| 3,349,338 A | 10/1967 | Sosin | |
| 4,278,176 A | 7/1981 | Adams | |
| 4,335,872 A * | 6/1982 | Caplis et al. | 269/43 |
| 4,349,338 A | 9/1982 | Heppler | |
| 4,383,615 A | 5/1983 | Aquino | |
| 4,657,138 A | 4/1987 | Watson | |
| 4,795,441 A | 1/1989 | Bhatt | |
| 4,850,484 A | 7/1989 | Denman | |
| 4,863,023 A | 9/1989 | Payne et al. | |
| 4,979,945 A | 12/1990 | Wade et al. | |
| 5,007,535 A | 4/1991 | Meseke et al. | |
| 5,013,299 A | 5/1991 | Clark | |
| 5,031,768 A | 7/1991 | Fischer | |
| 5,047,019 A * | 9/1991 | Sincock | 604/192 |
| 5,057,282 A * | 10/1991 | Linder | 422/547 |
| 5,104,375 A | 4/1992 | Wolf et al. | |
| 5,160,324 A | 11/1992 | Halbach | |
| 5,303,822 A | 4/1994 | Wengyn et al. | |
| 5,372,343 A | 12/1994 | Suzuki | |
| 5,435,448 A | 7/1995 | Kempen | |
| 5,850,917 A * | 12/1998 | Denton et al. | 206/366 |
| 6,202,862 B1 * | 3/2001 | Acquaviva et al. | 211/69.5 |
| 6,267,256 B1 * | 7/2001 | Thilly | 211/60.1 |
| 6,565,054 B2 | 5/2003 | Weesner et al. | |
| 6,595,362 B2 | 7/2003 | Penney et al. | |
| D479,329 S | 9/2003 | Sanquinetti | |
| 7,611,012 B2 | 11/2009 | Ross | |
| 8,196,741 B2 | 6/2012 | Finke et al. | |
| 8,485,357 B2 * | 7/2013 | Song et al. | 206/366 |
| 2013/0177381 A1 * | 7/2013 | Josef et al. | 414/802 |

* cited by examiner

*Primary Examiner* — Jacob K Ackun
(74) *Attorney, Agent, or Firm* — Craig W. Barber; Barber Legal

(57) ABSTRACT

A syringe holder body holds syringes in apertures passing through the rectangular body due to the action of a pliable layer within the holder body. The holder body may be transported between base units which have track bodies which hold the body locked in place when it is inserted therein. Latches and track arms provide more secure locking into place. Projecting from the bottom of the flat syringe holder body are syringe guards which protect the bottom end of the syringes and their needles.

10 Claims, 7 Drawing Sheets

MOBILE MULTIPLE SYRINGE HOLDER

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

CROSS-REFERENCE TO RELATED APPLICATIONS

N/A

FIELD OF THE INVENTION

This invention relates generally to syringe holders, and specifically to transportable syringe holders which hold multiple syringes.

STATEMENT REGARDING FEDERALLY FUNDED RESEARCH

This invention was not made under contract with an agency of the US Government, nor by any agency of the US Government.

BACKGROUND OF THE INVENTION

Emergency workers of many types, as well as hospital workers in high work load/high stress settings such as the emergency room, ambulances, air ambulances, and other medical personnel who's work requires them to move about a great deal all confront the problem of moving syringes and vials of medicine securely. In general, syringes are easily broken, have sharp needles protruding from one end and often need to be pre-loaded with medicines prior to the medical person moving about. Carrying a single syringe requires a nominal amount of attention under the best conditions, in stressful situations carrying a group of syringes can become slightly hazardous, both in terms of needle sticks/broken equipment and also in terms of loss of medicine which may be needed after a syringe break.

For example, an air nurse may receive a call and at the hospital may load up several syringes of different medicines prior to entering the helicopter and then flying to the location of the call for medical help. Leaving the hospital, entering the helicopter, leaving the helicopter at the call site and all the same steps on the return flight each represent another opportunity to damage a syringe in addition to the actual syringe handling necessary to treat the injured party.

To complicate matters, the space inside of a helicopter or other ambulance is quite limited, so there is not a great deal of space for organizing syringes.

It is of course possible to organize syringes inside of the hospital in a desk rack for example, however, upon departure the syringes must be pulled from the desk rack and put into some other type of storage (a drawer or the like) inside of the helicopter ambulance, and then pulled from that and reorganized if they are needed outside of the helicopter. Thus, various racks and devices are known in the prior art, but none of these items are known to be usable in multiple locations such as a hospital, a helicopter, an ambulance, on foot or attached to a clipboard.

Thus, it would be preferable to provide a mobile and transportable syringe holding device which can be used in multiple settings.

It would further be preferable to provide a device which protects the ends of syringes during transportation in the device.

It would further be preferable to provide a device which can be removed from installation in one location, transported and then be inserted into an installation in another location.

SUMMARY OF THE INVENTION

GENERAL SUMMARY

The present invention teaches a flat syringe holder body which holds syringes securely and safely in place while the syringe holder body itself is transported. The syringe holder body is then locked into place in a base unit which comprises a mounting plate and a track body. The track body passes around part or all of the edge/circumference of the syringe holder body and locks the body in place therein, in which mode the entire invention presents the appearance of a small shelf fixed in place. However, the syringe holder body may be removed from the track body of the base unit and conveyed, for example by hand, to another base unit, where it is then snapped into place in the new base unit.

The syringe holder body itself is an efficient design which protects the syringes therein with a minimum of weight and material, which is important in areas such as aircraft emergency services: the syringe holder body is a flat (planar) body with edges/planform matching the shape of the track body and its arms. The holder body also has a plurality of holes passing therethrough. The holes are large enough to admit a typical syringe. A median layer of the holder body is some material similar to rubber in that it is pliable and has a high coefficient of friction, and the holes are smaller as they pass through the pliable material, in fact they are slightly smaller than the diameter of a standard syringe. The result is that the syringe is gently forced into place through the hole in the pliable material, then held in place shielded from below by projecting syringe guards (shaped similar to shatter-proof test tubes) and shielded from the sides by the shatter-resistant holder body materials of the top and bottom layers. By this means, only the upper ends of the syringes are left accessible for medical personnel to use.

Using the device, a medical person may fill up syringes with desired medications, put the syringes into the holder body, and then using a one handed grip move the syringes safely from base unit to base unit. As an example, a flight nurse might have a first base unit in their office at a hospital, a second base unit on the edge of a clip board, a third base unit mounted in their helicopter, a fourth one in a ground ambulance, and thus be able to transport pre-loaded medications with great safety and convenience.

SUMMARY IN REFERENCE TO CLAIMS

It is therefore another aspect, advantage, objective and embodiment of the invention, in addition to those discussed previously, to provide a mobile syringe holder for use with syringes having a first diameter, the syringe holder comprising:

a planar syringe holder body having a generally flat body shape with edges and a planform defined by the edges, and having a top and a bottom, the flat body having at least one syringe aperture passing therethrough from top to bottom, the syringe aperture having a syringe guard attached thereto and projecting downward therefrom, the syringe guard having a substantially cylindrical body with a closed bottom end and an open top end, the syringe guard attached to the syringe aperture at the open top end; the syringe guard made of a shatter-resistant material;

the syringe holder body top being comprised of a top layer, the syringe holder bottom being comprised of a bottom layer, the top layer and bottom layer being shatter-resistant material;

the syringe holder body having disposed between the top and bottom layers a middle layer, the middle layer being comprised of a pliable material;

the syringe aperture having a first diameter which is at least equal to such syringe first diameter, the syringe aperture having the first diameter through the top and bottom layers;

the syringe aperture having a second diameter which is less than such syringe first diameter, the syringe aperture having the second diameter through the middle layer;

the top, middle and bottom layers fastened together with screws, a first base unit comprising;

a first track body, dimensioned and configured to mechanically engage to the edges of the syringe holder body and lock the syringe holder body in place in the first track body, the syringe holder body having a first mode locked in place in the first track body and a second mode free of the first track body;

a first mounting plate attached to and projecting from the track body and dimensioned and configured to be fastened in place.

It is therefore another aspect, advantage, objective and embodiment of the invention, in addition to those discussed previously, to provide a mobile syringe holder wherein the mounting plate further comprises:

at least one flat surface and a plurality of fastening holes passing through the mounting plate and adapted to receive fasteners therethrough.

It is therefore another aspect, advantage, objective and embodiment of the invention, in addition to those discussed previously, to provide a mobile syringe holder wherein the mounting plate further comprises: at least one flat surface and an adhesive on the flat surface.

It is therefore yet another aspect, advantage, objective and embodiment of the invention, in addition to those discussed previously, to provide a mobile syringe holder wherein the generally flat body shape further comprises: a rectangle.

It is therefore another aspect, advantage, objective and embodiment of the invention, in addition to those discussed previously, to provide a mobile syringe holder wherein the shatter-resistant material further comprises polymer.

It is therefore another aspect, advantage, objective and embodiment of the invention, in addition to those discussed previously, to provide a mobile syringe holder wherein the shatter-resistant material further comprises polycarbonate.

And it is therefore also an aspect, advantage, objective and embodiment of the invention, in addition to those discussed previously, to provide a mobile syringe holder wherein the syringe guard material is transparent.

It is therefore another aspect, advantage, objective and embodiment of the invention, in addition to those discussed previously, to provide a mobile syringe holder further comprising: a second base unit separate from the first base unit, the syringe holder having a third mode locked in place in the second base unit; whereby the syringe holder unit may be moved from one base unit to another base unit without removing the syringes therefrom.

It is therefore another aspect, advantage, objective and embodiment of the invention, in addition to those discussed previously, to provide a mobile syringe holder wherein the first track body further comprises: a pair of arms extending from and part of the first track body, the arms bearing latches by which means the first syringe holder body is locked into place in the first track body.

It is therefore another aspect, advantage, objective and embodiment of the invention, in addition to those discussed previously, to provide a mobile syringe holder wherein the pair of arms further comprise respective hinges allowing the arms to rotate relative to the first track body.

INDEX TO REFERENCE NUMERALS

Figure 1:
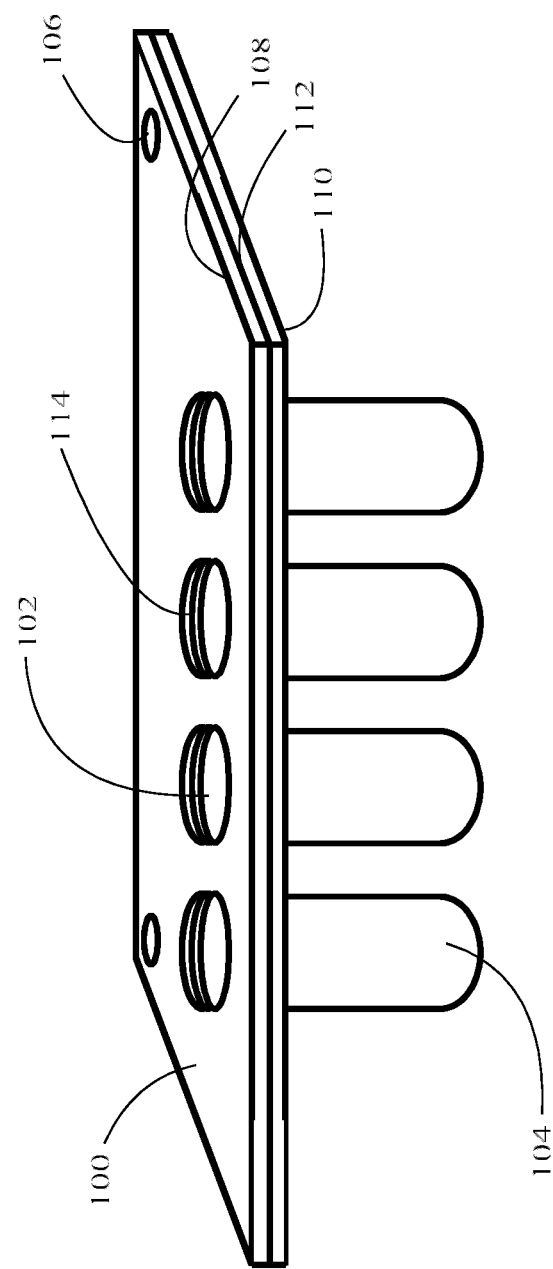
FIG. 1 is a perspective view of a first embodiment of the invention.

Syringe plate 100
Syringe aperture 102
Syringe guard 104
Connection hole 106
Top surface plate 108
Bottom surface plate 110
Pliable layer 112
Pliable ring 114
Syringe/vial plate 200
Syringe aperture 202
Connection point 206
Pliable ring 214
Pliable hole 216
Rounded corner 218
Syringe plate 300
Enclosure track 302
Latch 304
Arm 306
Track body 402
Mounting plate 404
Hinge/spring 406
Race inside of track 407
Fastener holes 408
Apertures 410
Arm 502
Latch 504
Diagonal hinge 505
Syringe guard 604
Top surface plate 608
Bottom surface plate 610
Pliable layer 612

DETAILED DESCRIPTION

FIG. 1 is a perspective view of a first embodiment of the invention, a planar syringe holder body. Syringe plate 100 has a plurality of syringe apertures 102, which number may vary. While five to six apertures is considered useful, lower or higher numbers may be usefully employed. Syringe guard 104 is an optional feature of the invention. A cylindrical body of sufficient size to accept at least the bottom end of a syringe, syringe guard 104 prevents damage to the needles and injection end of syringes at all times, especially during transit. Syringe guard 104 may advantageously be transparent, to allow visual inspection of the contents of the syringes without removing them from the device.

Connection hole 106 may advantageously be employed with the track body (described in referent to later figures), for example with bayonet-style attachment pins to hold the embodiment of FIG. 1 more securely in the base unit.

Top surface plate 108 and bottom surface plate 110 may provide the device with a shatter-resistant strength, and as such may be polycarbonate, other polymers, metal, wood, or the like.

Pliable layer 112 on the other hand will aid in retention of syringes within syringe apertures 102. At the point at which the aperture passes through the flat body 100, pliable ring 114 will be exposed. While in the embodiment of FIG. 1, the pliable ring 114 appears to be almost flat, this is not the preferred embodiment: a better view is obtained in FIG. 2.

Figure 2:
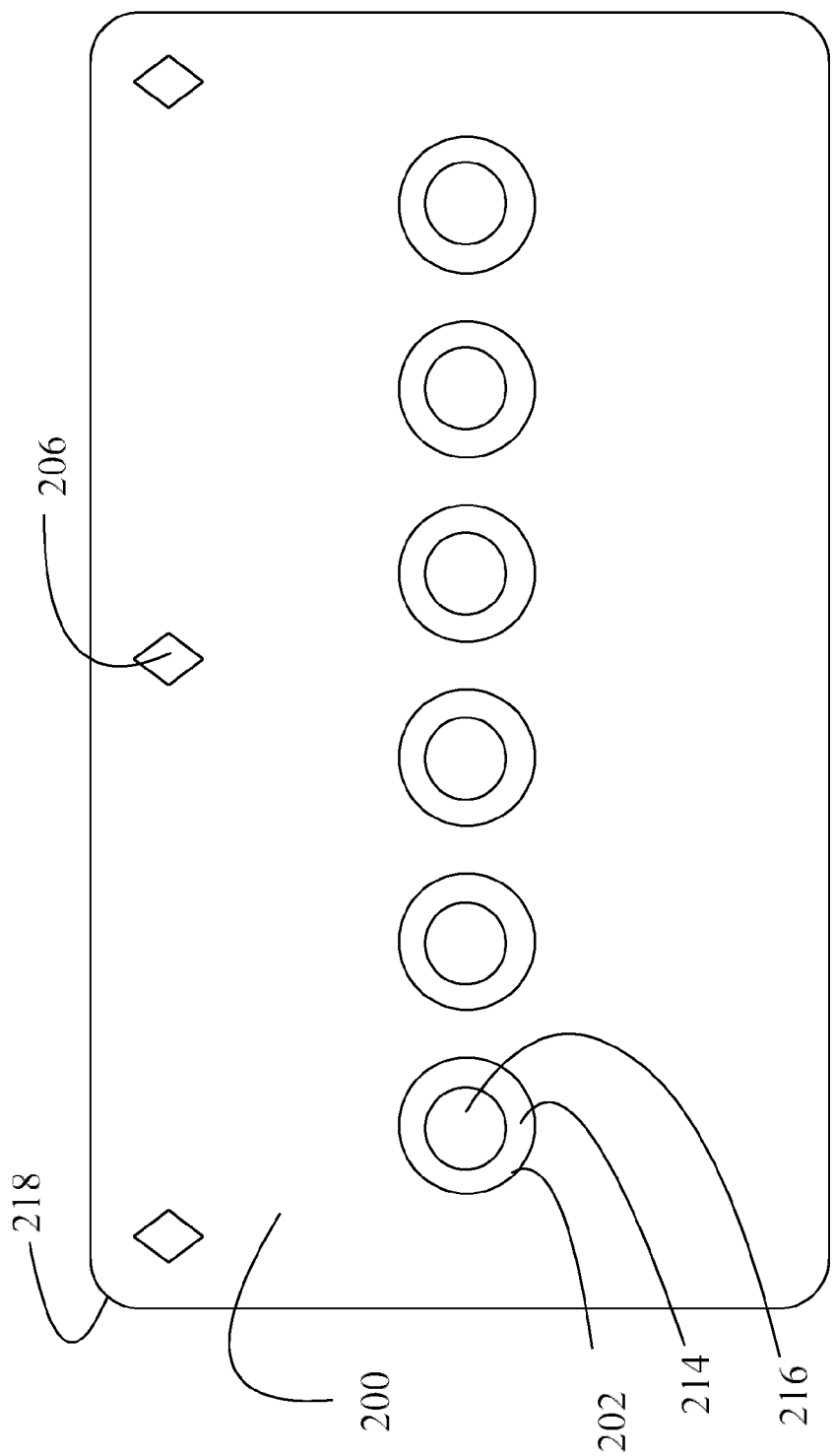
FIG. 2 is a top view of a second embodiment of the invention, showing more clearly the nature of the pliable layer in the syringe apertures.

FIG. 2 is a top view of a second embodiment of the invention, showing more clearly the nature of the pliable layer in the syringe apertures. Syringe/vial plate 200 has syringe aperture 202, a different arrangement of connection points 206 (which may be pins, locking devices, etc, in addition to holes) and more clearly visible than in FIG. 1, the width of pliable ring 214. Pliable ring 214 thus has pliable hole 216 which may advantageously have a diameter just smaller than a syringe diameter, so that when a syringe is passed through the hole 216, it "sticks" to the high-friction pliable material (such as rubber, latex, etc) of the pliable layer. By this means the syringe is maintained safely within the device.

It will also be seen that this embodiment has a different number of holes, six in this case, which is generally preferred as a reasonable number for an on-call mobile medical person.

Rounded corner 218 prevents accidents involving sharper corners, and further demonstrates that within the scope of the invention a number of arrangements of syringe holder planforms are contemplated.

Figure 3:
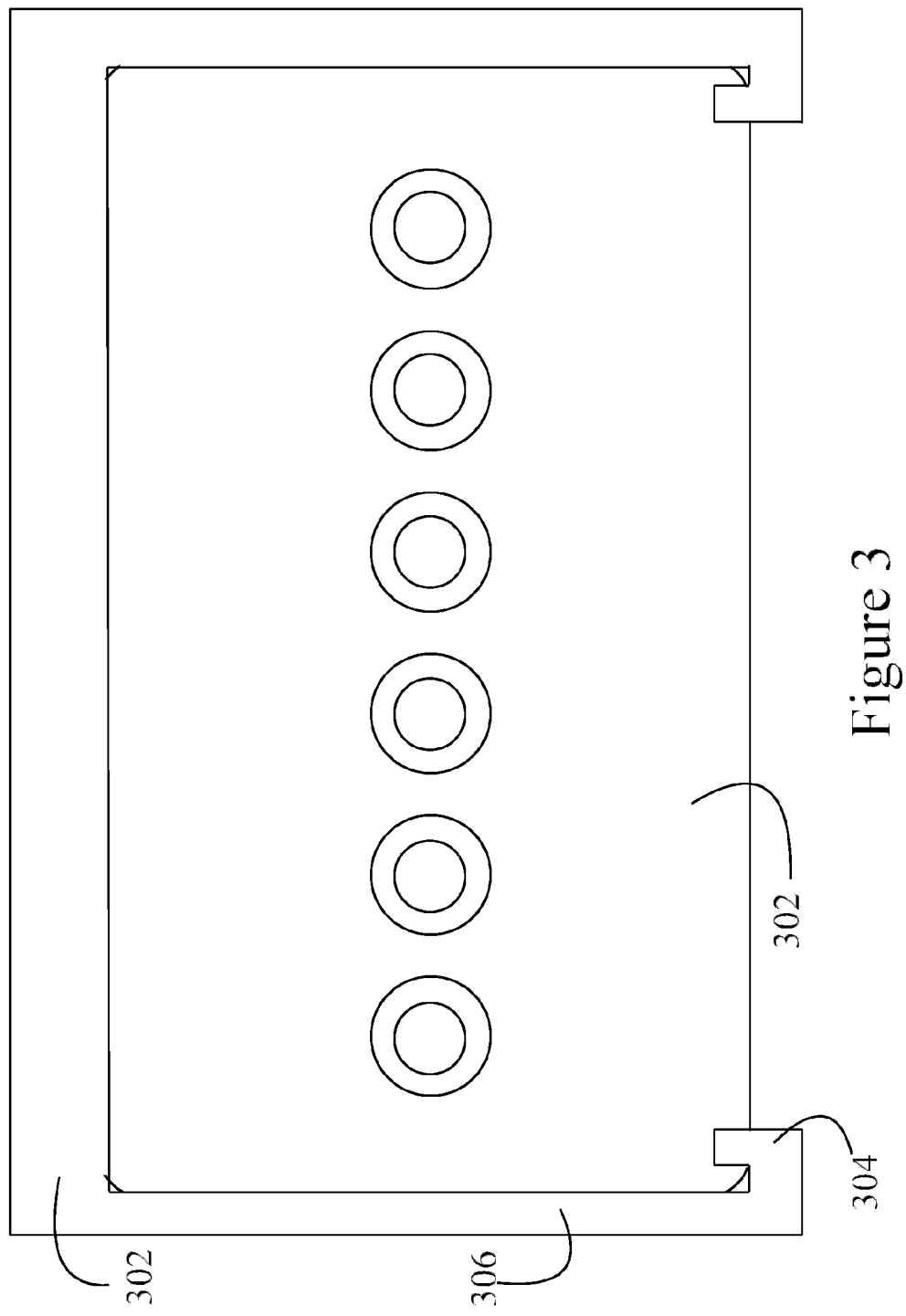
FIG. 3 is a top view of a third embodiment of the invention, showing the syringe plate locked into a track body.

FIG. 3 is a top view of a third embodiment of the invention, showing the syringe plate nearly locked into a track body. In the best mode and preferred embodiment now contemplated, the syringe plate 300 may be seen to be locked within the track body enclosure track 302 of the base unit. Latch 304 may open and close to secure the device in place, or the arms 306 may swivel, or the arms may be flexible so the syringe holder body 300 may lock into place without further mechanisms. In this particular embodiment, the arms are equipped with internal diagonal hinges so that the latch 304 may rotate with respect to the arm 306, and since it rotates at an angle, the result is that rotates into alignment with the arm in one direction but into a perpendicular angle with the arm if rotated in the other direction. FIG. 3 shows one latch in each position.

The significant feature displayed in FIG. 3 is that the syringe holder body 300 has two modes: it may be locked into place into a base unit as displayed in FIG. 3 or not, as in FIGS. 1 and 2.

Thus multiple base units can be used, such as one in an air ambulance and one in an office, and the holder body 300 merely transferred between them, always loaded with the syringes of medications.

Figure 4:
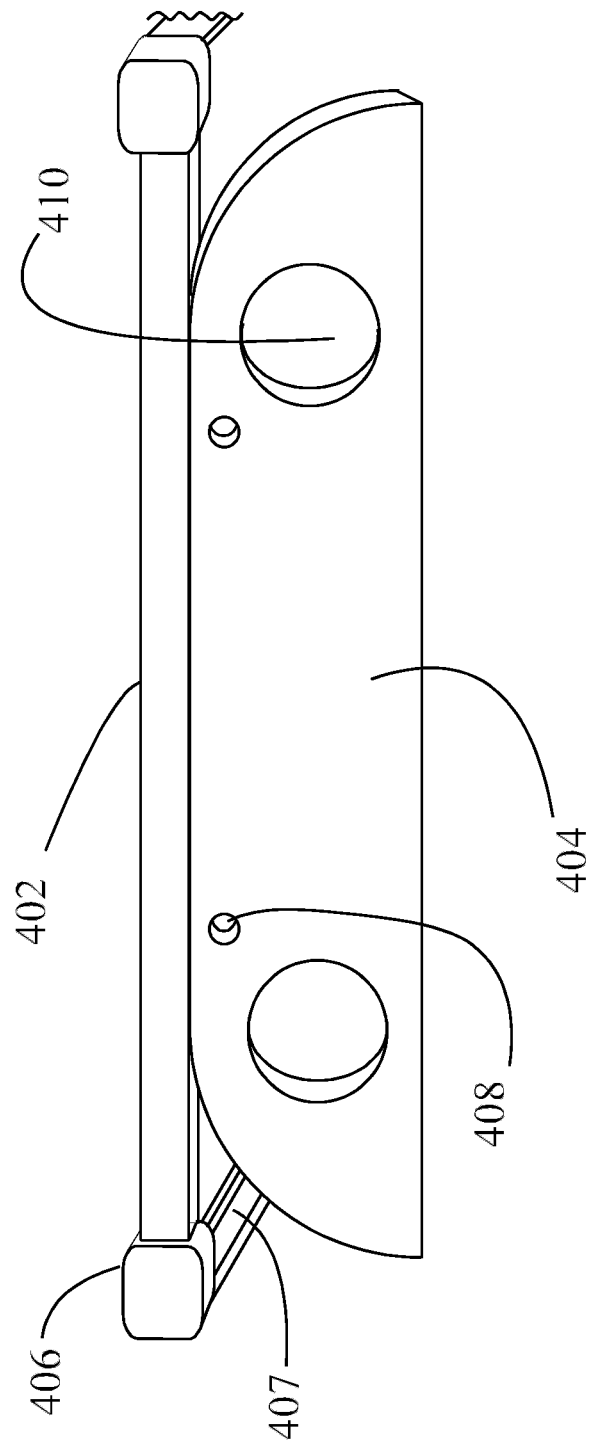
FIG. 4 is a perspective rear view of a fourth embodiment of the invention, with the latching arms raised.

FIG. 4 is a perspective rear view of a fourth embodiment of the invention, with the latching arms raised.

Track body 402 is shown edge on, so that mounting plate 404 may be seen. Hinge/spring 406 may also be seen, which in this embodiment allows the arms to rotate in relationship to the track body.

Fastener holes 408 may be dimensioned and configured to accept standard fasteners such as nails, bolts, screws, brads, tacks and so on. Apertures 410 may also be seen. These apertures may connect to universal connectors, or to the retaining tracks seen in helicopter ambulances.

On the inside of the arm, a race 407 (a long groove on the inside of the arm) may be seen: this groove allows a syringe body to be inserted into the arm and retained securely.

Figure 5:
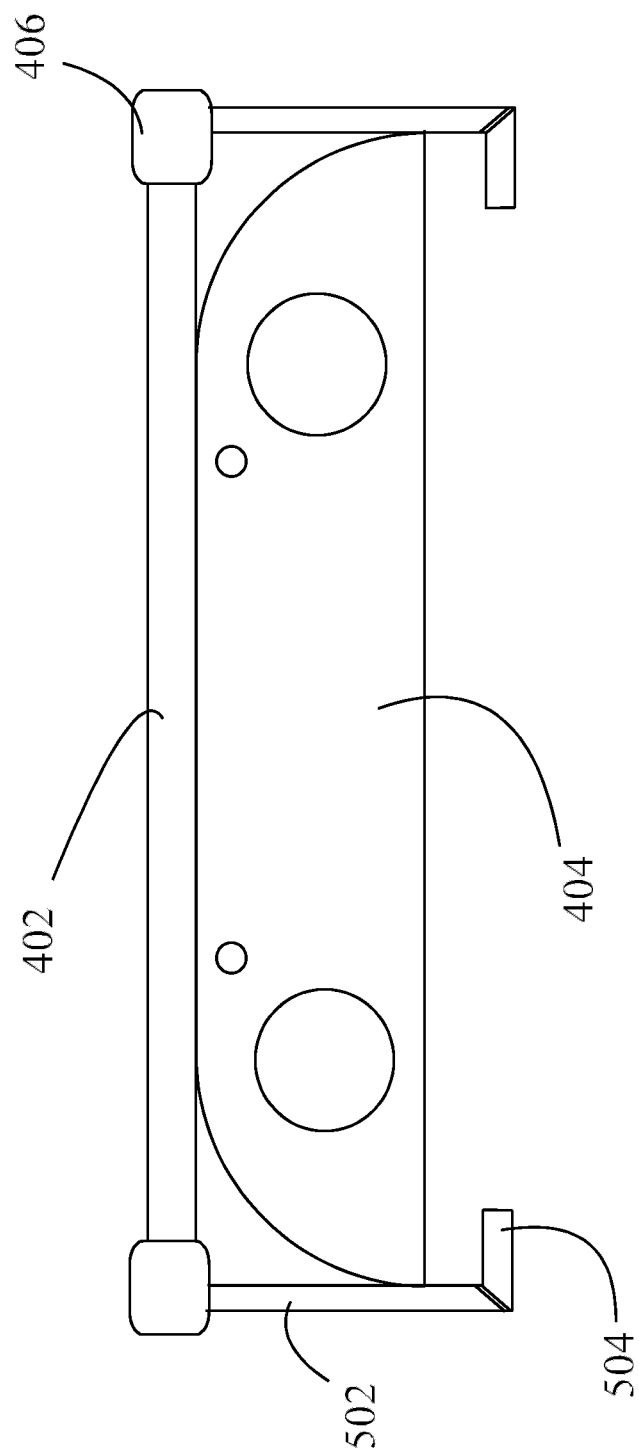
FIG. 5 is a rear view of the fourth embodiment of the invention with the latching arms lowered.

FIG. 5 is a rear view of the fourth embodiment of the invention with the latching arms lowered. Arm 502 and latch 504 are seen hanging downward, out of the plane of the syringe holder (not seen), so the syringe holder may be freely removed or inserted.

Figure 5B:
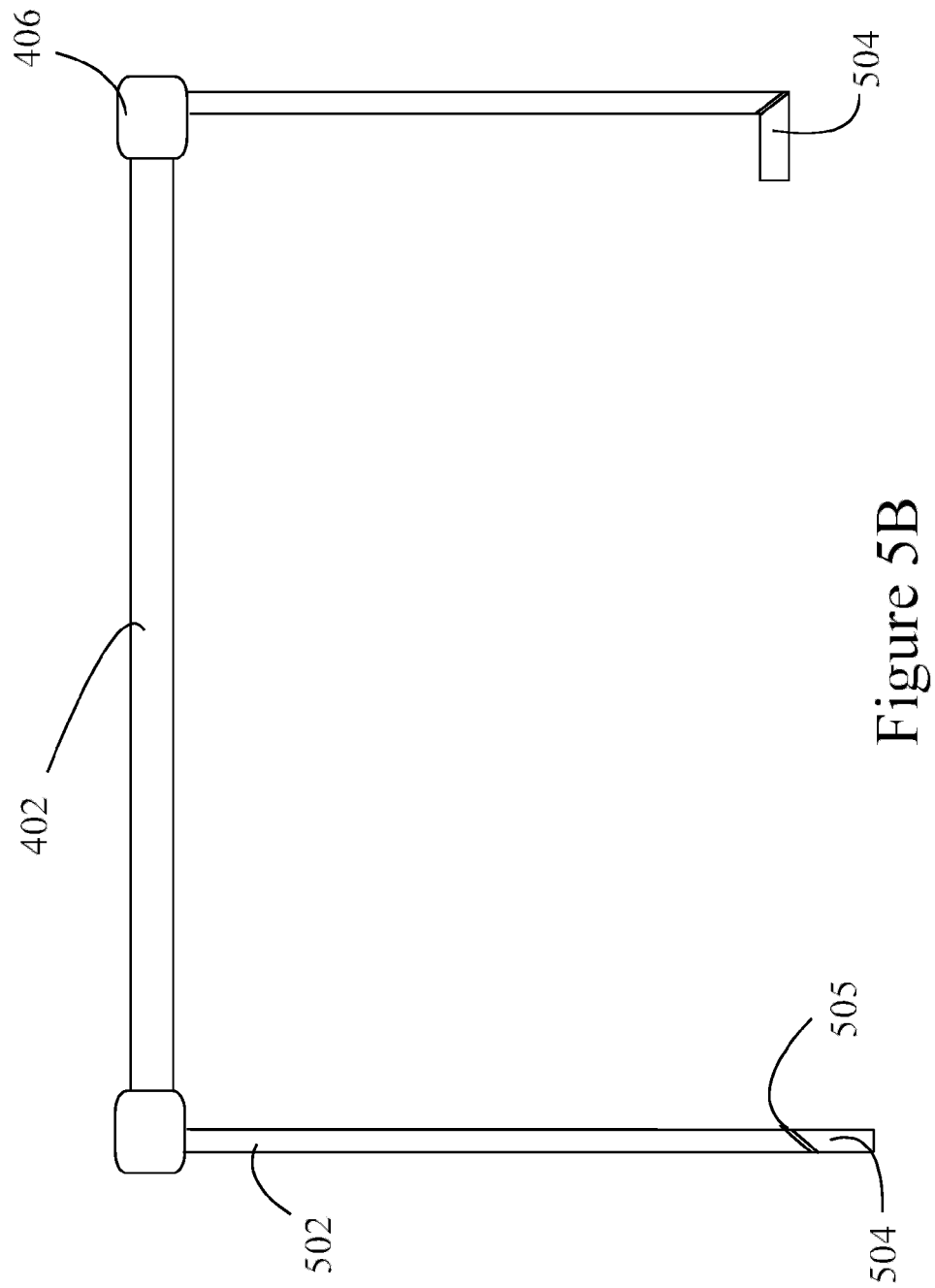
FIG. 5B is a top view of a fifth embodiment of the track of the invention, showing the track without the syringe holder body in place.

FIG. 5B is a top view of a fifth embodiment of the track of the invention, showing the track without the syringe holder body in place. Again, one latch 504 is shown rotated on diagonal hinge 505 into the "open" position in which it is in line with the rest of arm 502 while the other latch is shown rotated perpendicular to the arm, as it would be if a syringe body were inserted and the latch used to secure it in place.

Figure 6:
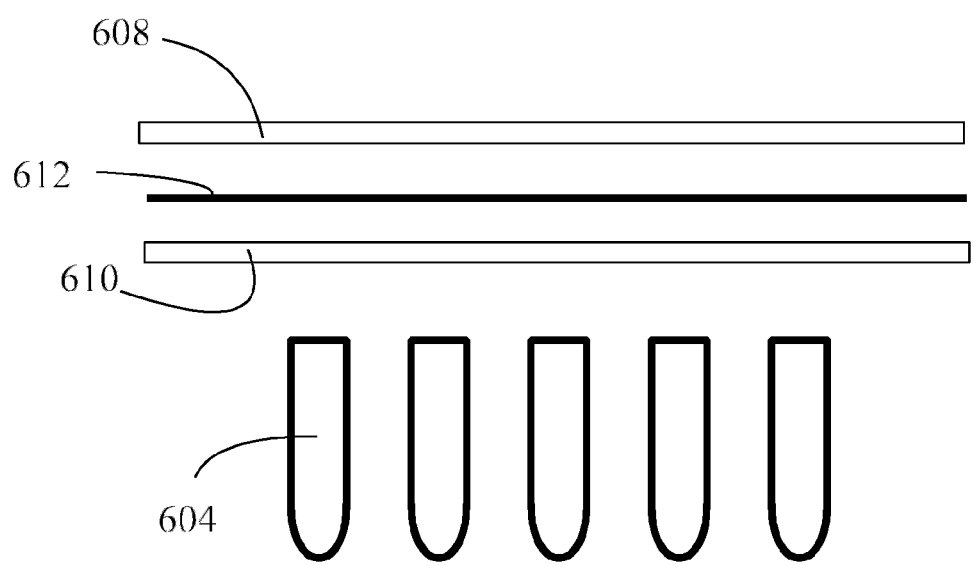
FIG. 6 is a front exploded view of a fifth embodiment of the invention showing the layers of material and the syringe guards.

FIG. 6 is a front exploded view of a fifth embodiment of the invention showing the layers of material and the syringe guards.

Syringe guard 604 is more easily seen, and the difference between the top surface plate 608, bottom surface plate 610 and pliable layer 612 is also seen. The different layers may be fastened together with screws, other fasteners, adhesives, polymer weld, or the like.

The disclosure is provided to allow practice of the invention by those skilled in the art without undue experimentation, including the best mode presently contemplated and the presently preferred embodiment. Nothing in this disclosure is to be taken to limit the scope of the invention, which is susceptible to numerous alterations, equivalents and substitutions without departing from the scope and spirit of the invention. The scope of the invention is to be understood from the appended claims.

What is claimed is:

1. A mobile syringe holder for use with syringes having a first diameter, the syringe holder comprising:
   a planar syringe holder body having a generally flat body shape with edges and a planform defined by the edges, and having a top and a bottom, the flat body having at least one syringe aperture passing therethrough from top to bottom,
   the syringe aperture having a syringe guard attached thereto and projecting downward therefrom, the syringe guard having a substantially cylindrical body with a closed bottom end and an open top end, the syringe guard attached to the syringe aperture at the open top end; the syringe guard made of a shatter-resistant material;
   the syringe holder body top being comprised of a top layer, the syringe holder bottom being comprised of a bottom layer, the top layer and bottom layer being shatter-resistant material;

the syringe holder body having disposed between the top and bottom layers a middle layer, the middle layer being comprised of a pliable material;

the syringe aperture having a first diameter which is at least equal to such syringe first diameter, the syringe aperture having the first diameter through the top and bottom layers;

the syringe aperture having a second diameter which is less than such syringe first diameter, the syringe aperture having the second diameter through the middle layer;

the top, middle and bottom layers fastened together with screws;

a first base unit comprising;

a first track body, dimensioned and configured to mechanically engage to the edges of the syringe holder body and lock the syringe holder body in place in the first track body, the syringe holder body having a first mode locked in place in the first track body and a second mode free of the first track body;

a first mounting plate attached to and projecting from the track body and dimensioned and configured to be fastened in place.

2. The mobile syringe holder of claim 1, wherein the mounting plate further comprises:

at least one flat surface and a plurality of fastening holes passing through the mounting plate and adapted to receive fasteners therethrough.

3. The mobile syringe holder of claim 1, wherein the mounting plate further comprises:

at least one flat surface and an adhesive on the flat surface.

4. The mobile syringe holder of claim 1, wherein the generally flat body shape further comprises: a rectangle.

5. The mobile syringe holder of claim 1, wherein the shatter-resistant material further comprises polymer.

6. The mobile syringe holder of claim 1, wherein the shatter-resistant material further comprises polycarbonate.

7. The mobile syringe holder of claim 1, wherein the syringe guard material is transparent.

8. The mobile syringe holder of claim 1, further comprising: a second base unit separate from the first base unit, the syringe holder having a third mode locked in place in the second base unit; whereby the syringe holder unit may be moved from one base unit to another base unit without removing the syringes therefrom.

9. The mobile syringe holder of claim 1, wherein the first track body further comprises: a pair of arms extending from and part of the first track body, the arms bearing latches by which means the first syringe holder body is locked into place in the first track body.

10. The mobile syringe holder of claim 9, wherein the pair of arms further comprise respective hinges allowing the arms to rotate relative to the first track body.

* * * * *